United States Patent [19]

Dolhyj et al.

[11] 4,077,912

[45] Mar. 7, 1978

[54] CATALYSTS USEFUL FOR EXOTHERMIC REACTIONS

[75] Inventors: Serge R. Dolhyj, Parma; Ernest C. Milberger, Solon, both of Ohio

[73] Assignee: Standard Oil Company, Cleveland, Ohio

[21] Appl. No.: 296,759

[22] Filed: Oct. 12, 1972

[51] Int. Cl.$^2$ .............................................. B01J 35/02
[52] U.S. Cl. ...................... 252/461; 252/454; 252/455 R; 252/463; 252/477 R; 427/215
[58] Field of Search .................. 252/477 R, 454, 461, 252/455 R, 463, 448; 117/16, 100 S, 109, 100 B; 428/403

[56] References Cited

U.S. PATENT DOCUMENTS

| | | | |
|---|---|---|---|
| 2,355,831 | 8/1944 | Voorhees | 252/465 X |
| 3,087,828 | 4/1963 | Linton | 117/100 S |
| 3,251,714 | 5/1966 | Rotschild | 117/100 B |
| 3,274,019 | 9/1966 | La Vine | 117/16 |
| 3,420,784 | 1/1969 | Keith et al. | 252/477 R |
| 3,473,943 | 10/1969 | Kai | 117/16 |
| 3,513,109 | 5/1970 | Stiles | 252/477 R |
| 3,554,929 | 1/1971 | Aarons | 252/477 R |
| 3,562,185 | 2/1971 | Friedrichsen et al. | 252/477 R |
| 3,563,913 | 2/1971 | De Krijger et al. | 252/477 R |
| 3,565,830 | 2/1971 | Keith et al. | 252/477 R |
| 3,615,166 | 10/1971 | Hindin et al. | 252/477 R |
| 3,637,529 | 1/1972 | Van Beek et al. | 252/473 X |
| 3,671,432 | 6/1972 | Peters et al. | 252/464 X |
| 3,681,260 | 8/1972 | Foucher et al. | 252/477 R |
| 3,723,353 | 3/1973 | Eurlings et al. | 252/474 X |

FOREIGN PATENT DOCUMENTS

1,220,105  1/1971  United Kingdom ................. 252/461

OTHER PUBLICATIONS

Kirk–Othmer, Encyclopedia of Chemical Technology, Second Edition, vol. 4, John Wiley & Sons, New York, pp. 567–568 (1964).

*Primary Examiner*—W. J. Shine
*Attorney, Agent, or Firm*—David J. Untener; Herbert D. Knudsen; Larry W. Evans

[57] ABSTRACT

Catalysts which are excellent for exothermic reactions have been discovered. These catalysts consist of an essentially inert support having a strongly adherent outer coating of active catalytic material.

11 Claims, 2 Drawing Figures

CATALYSTS USEFUL FOR EXOTHERMIC REACTIONS

BACKGROUND OF THE INVENTION

The use of supports for catalysts is well known in the art. In a traditional sense, the support is normally considered to be a very small particle that provides a base for the active catalytic material. This supported catalyst is then agglomerated to provide a tablet having an essentially uniform catalyst composition throughout. The present invention is different from this art in that a massive support is employed, and a nonhomogeneous catalyst composition is obtained.

Supports have been impregnated with slurries, see for example, U.S. Pat. No. 3,172,893. The use of such slurries "impregnates" the support material rather than coating the material, see column 3, lines 46-48.

Transition metal oxide catalysts have been prepared by adsorption of water on a support and mixing the transition metal oxide with the support in a blender to effect a homogenization of the catalytic oxide on the support, see U.S. Pat. No. 3,671,432.

The essentially inert support materials used in the invention are commercially available or they can be conveniently prepared. U.S. Pat. No. 3,145,183 shows the preparation of support balls that are useful in the preparation of the catalysts of the invention. Also, suitable support materials can be prepared by compacting a suitable support material into the desired shapes.

Active catalytic materials of special interest in the present invention are known. Idol in U.S. Pat. No. 2,904,580 shows catalysts containing the oxides of bismuth and molybdenum. Sennewald in U.S. Pat. No. 3,226,422 shows catalysts containing the oxides of iron, bismuth, phosphorus and molybdenum. Grasselli, Miller and Hardman in U.S. Pat. No. 3,642,930 show catalysts containing the oxides of an alkali metal, bismuth, iron and molybdenum and reactions with these catalysts.

Catalysts containing the oxides of molybdenum, vanadium and tungsten are shown by Yamaguchi et al. in U.S. Pat. No. 3,567,773, and Belgium Pat. Nos. 775,251 and 774,329. These catalysts are normally employed in strongly exothermic reactions.

A third set of catalysts contain at least the oxides of antimony and molybdenum. These catalysts are shown in the oxidation reactions in U.S. application Ser. No. 67,269 filed Aug. 26, 1970, now abandoned; Ser. No. 177,105 filed Sept. 1, 1971, now U.S. Pat. No. 3,907,834 and Ser. No. 250,660 filed May 5, 1972, now U.S. Pat. No. 3,904,653.

The invention is not the nature of the active catalytic material nor the nature of the particular support material, but the invention is the specific combination of these two aspects of the catalyst in such manner that a catalyst which is especially desirable for strongly exothermic reactions is obtained.

Difficulties with a fixed bed exothermic reaction are well known. The basic problem is that the heat generated cannot be dissipated by normal heat transfer techniques. Accordingly, the temperature of the reaction cannot be controlled. Also, "hot spots" in the reaction develop where no useful reaction occurs. The present invention is designed to alleviate these problems by a new catalyst that can be conveniently prepared.

SUMMARY OF THE INVENTION

It has now been discovered in the present invention that strongly exothermic reactions are more readily controlled by the use of a catalyst which comprises (a) an inert support of at least about 20 microns in diameter, said support having an outer surface, and (b) a coating of a catalytically active material on the outside surface of the support which strongly adheres to the outer surface of the support. These catalysts are conveniently prepared and make it possible to conduct strongly exothermic reactions in a fixed bed reactor with greater ease.

DESCRIPTION OF THE DRAWING

The catalysts of the invention are illustrated in the Figures.

DETAILED DESCRIPTION OF THE INVENTION

Figure 1:
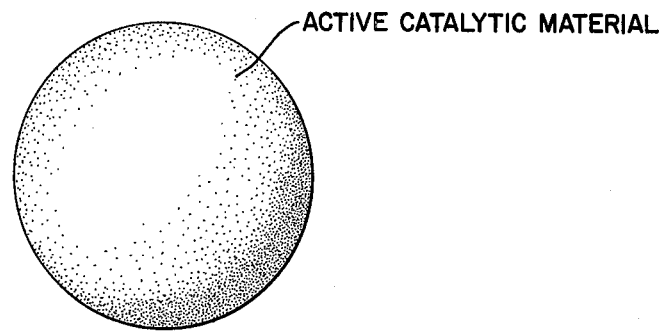
FIG. 1 shows a view of the catalyst of the present invention. The catalyst is a sphere with the entire outer surface of the sphere being the active catalytic material.
Figure 2:
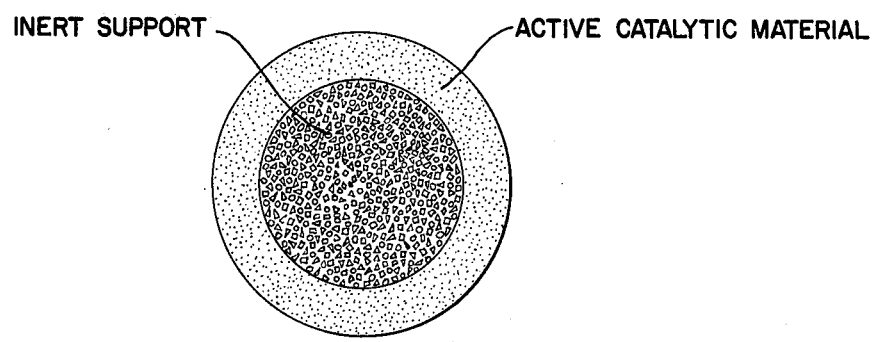
FIG. 2 shows a cross-sectional view of the spherical catalyst of FIG. 1 obtained by cutting the spherical catalyst in half. The catalysts consist of an inner core of the inert support and an outer coating of the active catalytic material. As can be readily seen from FIG. 2, the active catalytic material is distributed on the outside of the support and is not distributed uniformly throughout the tablet or impregnated into the tablet. Of course, it is true that in a small zone between the interface of the active catalytic material and the support there probably is some comingling of the two solids, but this zone is extremely narrow.

The components of the catalyst are not new and may be selected from a wide variety of materials that are known in the art. As noted, the catalyst of the present invention normally contains two discrete parts—an essentially inert support and an active catalytic material.

The essentially inert support may be selected from a wide choice of materials available in the art. This support material is massive and must have a diameter of at least about 20 microns. Preferred supports have a diameter of about 1/32 inch to about ½ inch, but there is no limitation on the size of the support material.

The support material must be at least partially porous. By this is meant the support material must be susceptible to the penetration of liquid. Preferred support materials are capable of adsorbing at least about 5% by weight of water based upon the weight of the support.

In a reactor one of the important variables is the pressure drop. The present invention can be utilized to minimize the pressure drop by the use of spherical catalysts. These spherical catalysts can be prepared by using a spherical support material and distributing the active catalytic material evenly on the outer surface of the support.

Even though any support material could be used in the present invention, certain support materials are preferred. The preferred support materials include silica, alumina, alumina-silica, silicon carbide, titania and zirconia. Especially preferred among these supports are silica, alumina and alumina-silica.

The second component of the catalyst of the present invention is the catalytically active material. This material is not novel in the present invention for these catalysts and their preparations are described in the art as shown by the references cited in the Background of the Invention. Essentially any catalytic material may be used in the catalysts of the invention. Even though the class of catalysts is essentially unlimited, experience has shown that the present invention is especially adaptable to the use of catalysts containing catalytically active metal oxides. Thus, use of the present invention to prepare metal oxide catalysts or catalyst precursors that are converted to oxide catalysts are preferred.

In the present invention the preferred catalysts contain in the active catalytic component oxides of alkali metals, alkaline earth metals, V, Cr, Mo, W, Mn, Fe, Co, Ni, Cu, Zn, In, Tl, Sn, Sb, Bi, P and As. Preferred among these catalysts are those which contain at least the oxides of antimony and molybdenum. Also preferred are those catalysts which contain active components of the catalyst including at least the oxides of vanadium, tungsten and molybdenum. A third class of catalysts that are important are those catalysts which contain at least the oxides of bismuth and molybdenum.

The catalysts may contain essentially any proportions of support and catalytically active material. The limits on this relationship are only set by the relative ability of the catalyst and support material to accommodate each other. Preferred catalysts contain about 10 to about 100 percent by weight of catalytically active material based on the weight of the support.

One very intriguing aspect of the present invention is the possibility of coating the catalyst with two or more specific catalysts. Using the proper reactions and selective catalysts, two reactions could be conducted simultaneously or alternately to increase the utility of the reactor.

Now that the particular components of the catalyst have been described, the preparation of these catalysts can be considered. The preparation of these catalysts can be accomplished by various techniques. The basic method of preparing these catalysts is to partially wet the support material with a liquid. The support cannot be wet on the outside surface of the total mass. It should be dry to the touch. If the support is wet, then the active catalytic material will agglomerate into separated aggregates when coating of the support is attempted. These partially wet supports are then contacted with a powder of the catalytically active material and the mixture is gently agitated until the catalyst is formed.

The gentle agitation is most conveniently conducted by placing the partially wet support in a rotating drum and adding the active catalytic material until none is taken up by the support. This is very economically done.

The liquid used to wet the support may include inorganic or organic liquids and is essentially dependent upon the type of catalytically active material employed. The liquid and the catalytically active material must have a relatively high degree of attraction for each other. For example, if a hydrophylic catalytically active material is used, water may be used to wet the support. On the other hand if a hydrophobic catalytically active material is used, an organic solvent such as petroleum ether could be used. Water is the preferred liquid.

More specifically, the catalyst of the invention is prepared by (a) contacting an essentially inert support of at least about 20 microns in diameter with an excess of liquid in such manner that the liquid is adsorbed by the support to produce a wet support, (b) drying said wet support to produce a partially wet support, which partially wet support is defined as one that does not have the appearance of liquid on the outer surface of the support, but has at least some liquid adsorbed on the support, (c) contacting the partially wet support with a powder of a catalytically active material having a particle size of less than about 500 microns, and (d) gently agitating the mixture of the partially wet support and catalytically active material to produce the catalyst. It can be readily seen that the first two steps could be combined by the addition of a measured amount of liquid that would give a partially wet support. Thus, there would be no need for the intermediate drying step.

After the above steps have been taken in the catalyst preparation, other drying and activation steps can be used to produce the desired catalysts. These steps are known in the art and are not significantly altered by the present invention.

The present invention, however, does combine the catalytically active material and support material in a manner that provides an especially effective catalyst for strongly exothermic reactions.

SPECIFIC EMBODIMENTS

COMPARATIVE EXAMPLE A & B AND EXAMPLE 1.

Catalyst comparison in maleic anhydride reaction.

Active catalytic material having the formula $SbMo_3V_{0.1}O_x + W_{0.06}$ was prepared. The catalyst was run in parallel reactions to produce maleic anhydride from butadiene using a reactor of a ⅜ inch stainless steel tube containing 20 cc. of catalyst. The butadiene-to-air ratio was 1 to 21 and the contact time was 3.3 seconds. The remaining process conditions and results are given in Table I.

The catalyst of Comparative Example A was used as pure active catalytic material. The catalyst of Comparative Example B was pure active catalyst physically mixed with 40% silica. The catalyst of Example 1 was a coated catalyst of the invention wherein 40% by weight of the catalyst of Comparative Example B based on the weight of the support was coated on ⅛ inch diameter silica spheres.

The coated catalyst was prepared by adding four grams of water to 50 grams of silica spheres and slowly adding 20 grams of the powdered (through 160 mesh) active catalytic material to the partially wet silica spheres while rotating the spheres in a glass jar rotated about a slightly inclined angle from horizontal. This rotating action provides sufficient agitation so that the active catalytic material forms a substantially uniform coating on the silica support. The active catalyst did not permeate the support.

The exotherm was recorded for each of the reactions by recording the bath temperature and recording the temperature in the center of the reactor using a thermowell. The results using these catalysts are described in Table I.

TABLE I

| | Comparison of Coated Catalyst of the Invention with Catalysts of the Art | | | |
|---|---|---|---|---|
| | | Temp. ° F. | | |
| Example | Form of Catalyst | Bath | Thermowell | Exotherm |
| Comp. A | 100% active | 680 | 746 | 66 |
| Comp. B | 60% active 40% silica | 690 | 760 | 70 |
| 1 | Coated | 750 | 760 | 10 |

The data in Table I shows that the exotherm is reduced more than six-fold using coated catalysts.

COMPARATIVE EXAMPLE C AND EXAMPLES 2-5.

Different percentage coating.

A catalyst of $SbMo_3Fe_{0.2}V_{0.1}O_x + W_{0.06}$ was prepared by heating an aqueous slurry of $MoO_3$, $V_2O_5$, $Fe_2O_3$ and W metal and subsequently adding $Sb_2O_3$. The slurry was then double-drum dried at a drum surface temperature of 255°–260° F. The dried material contained 0.55% moisture. The product was 24.1% on 30 mesh screen, 40.9% through 30 and on 50 mesh screen and 35.0% through 50 mesh screen.

The support selected was ⅛ inch Alundum balls sold by Norton Chemical Company under the trade designation SA203. The balls were soaked in water at room temperature for 15 minutes and dried by placing them on a paper towel. 10.6 Grams $H_2O$/100 Grams of support was taken up. This was designated as 100% adsorption, the dry support being 0% adsorption. Using a hot-air gun, portions of the spheres having 100% adsorption were dried to give supports having 75% $H_2O$ adsorption, 50% adsorption and 25% adsorption.

The catalysts of the invention were prepared by the technique described in the examples above. The partially wet support was rotated in a glass jar and the active catalytic material was added until no further active catalyst was being taken up. The catalyst was dried overnight at 110° C. and was then shaken gently on a 20 mesh screen and any adhering fines of active were immediately removed.

The attrition resistance of the catalysts was determined by weighing the catalyst and then vigorously agitating the catalyst prepared above on a 20 mesh screen for three minutes. The loss in weight was considered to be loss in active material. The percent loss of active catalyst was determined by subtracting the final weight of active catalyst material in the catalyst from the original weight of the active catalyst, dividing by the original weight of the active catalyst and multiplying by 100.

Comparative Example C shows an undesirable catalyst preparation where a dry support was used. The attrition resistance of this catalyst is unacceptable.

The percent water adsorptions, weight of active before and after the attrition resistance test and the percent loss of active catalyst in the attrition resistance test are shown in Table II.

Upon cutting the catalysts of the invention in half, it was observed that the alundum spheres were not impregnated with the catalyst, but that it only contained a coating of active catalyst on the surface. After 1000 hours of use in the making of maleic anhydride, this outer coating was still retained without diffusion of the active material.

TABLE II

| | Catalysts Prepared from Supports Using Different $H_2O$ Adsorptions | | | |
|---|---|---|---|---|
| | $H_2O$ Adsorp., % | Weight Active/25 g. Support | | % Wt. Loss |
| Example | | As Prepared | After Attrition Test | |
| Comp. C | 0 | 4.48 | 2.12 | 53 |
| 2 | 25 | 6.82 | 4.78 | 29.9 |
| 3 | 50 | 14.20 | 12.98 | 8.6 |
| 4 | 75 | 24.08 | 22.40 | 7.0 |
| 5 | 100 | 24.42 | 23.80 | 2.5 |

Thus, it can be seen from the data in Table II that highly attrition resistant catalysts with large percentages of active catalytic material can be prepared by the process of the invention.

EXAMPLE 6

Preparation of a catalyst containing Bi and Mo in the active catalyst.

In the same manner as shown in the examples above, an active catalyst of 87.3% $K_{0.1}Ni_{2.5}Co_{4.5}Fe_3BiP_{0.5}Mo_{12}O_x$ and 12.7% $SiO_2$ was used to coat 10–30 mesh Alundum (SA203). The Alundum was wet with water to a 75% water adsorption, and the active catalyst having a size of less than 200 mesh was coated uniformly on the surface of the spheres to give a coating of 50% based on the weight of the support. The catalyst was observed to be attrition resistant. The catalyst was used in a 20 cc. fixed bed reactor to oxidize propylene to acrolein using air in a ratio of 8.9 volumes of air per volume of propylene. At a temperature of 700° F., the per pass conversion to acrolein was 82.0%. The conversion of propylene was 88.1% and the selectivity was 95.5%. Only a 10° F. exotherm was noted. Using pure active catalyst, the exotherm is normally about 25° F.

COMPARATIVE EXAMPLES D AND E AND EXAMPLES 7 AND 8

Effect of coated catalyst on oxidation of acrolein.

Active catalyst having the formula $W_{1.2}V_3Mo_{12}O_x$ was prepared and used to coat through 10 on 30 mesh Alundum shown above. The Alundum was wet to the 75% water adsorption level and 50 weight percent of active catalyst based on the weight of the support was coated uniformly on the surface of the Alundum. The catalyst was used in the oxidation of acrolein to acrylic acid in a 20 cc. reactor, and it was found that the exotherm was less than half the exotherm noted when pure active catalyst was used.

The experiments were conducted reacting acrolein/air/nitrogen/water in the ratios ⅛/2.8/8. The apparent contact time was 5.2±0.2 seconds. All of the acrolein reacted in each case. The results are shown in Table III.

TABLE III

| | Acrolein to Acrylic Acid — Effect of Coated Catalyst as Compared to Pure Active Catalyst | | | |
|---|---|---|---|---|
| | | Temp., ° F. | | |
| Example | Catalyst | Bath | Thermowell | Exotherm |
| Comp. D | 100% active | 500 | 516 | 16 |
| 7 | Coated | 500 | 507 | 7 |
| Comp. E | 100% active | 550 | 568 | 18 |
| 8 | Coated | 550 | 557 | 7 |

Thus, it can be seen in the parallel experiments above that the exotherm is significantly reduced by using the coated catalyst.

EXAMPLE 9

Coated catalyst in the oxidative dehydrogenation of 2-butene.

In the same manner as described above, through 10 on 20 mesh Alundum was coated with the active catalyst of Example 6. This catalyst was placed in a 20 cc. fixed bed reactor, and a feed of 21.9 volumes of air per volume of 2-butene was passed over the catalyst at a bath temperature of 700° F. The conversion of 2-butene was 93.7%, and the molar per pass conversion to butadiene was 77.2%. The exotherm noted was only 2° F. Normally, the exotherm for this reaction is much higher.

EXAMPLE 10

Effect of coated catalyst in large reactor.

A ¾ inch diameter pipe 9.5 feet long was filled with tablets of the active catalyst shown in Example 6. A coated catalyst was prepared from the active catalyst in Example 6 and ⅛ inch spherical Alundum to give a coating of about 50 weight percent active catalyst based on the weight of the support.

The reaction of 2-butene to butadiene was conducted under essentially identical conditions at a bath temperature of 700° F., a pressure of 20 psig and conversions of 94±2%. The feed when the pelleted active catalyst was used, however, was diluted with 15 moles of $N_2$ per mole of olefin. The exotherm noted with the coated catalyst was 18° F., whereas the exotherm of the pelleted catalyst was 65° F. even with the nitrogen dilution. This shows the surprising ability of the catalysts of the invention to control exotherms in exothermic reactions.

EXAMPLE 11

Effect of coated catalyst on the ammoxidation of propylene.

In a 20 cc. reactor the coated catalyst of Example 6 was used in the ammoxidation of propylene. The propylene/air/$NH_3$ feed was 1/11.3/1.12. No steam was fed. The exotherm conducting the reaction at a bath temperature of 805° F. was 22° F. The molar per pass conversion to acrylonitrile was 68.8% and the conversion of the propylene was 83.6%. In similar reactions with pure active catalyst or normal supported catalysts, steam dilution is necessary and the exotherm is much higher.

In the same manner as shown by the examples above, other active catalytic materials may be coated on Alundum spheres. For example, active catalysts containing the oxides or nitrates of FeBiPMo, BiPMo, SnWSbMo, PSbMo, SbSnVWMo and CuCrVWMo could be used as the active catalytic material.

Also in the same manner as shown by the examples above, other inert supports could be used as the material which is coated. For example, silicon carbide, zirconia or titania could be used to prepare the catalyst of the invention.

Catalysts of the invention could also be prepared by using different sized support. For example, a 20 micron silica support could be coated with a catalyst containing at least the oxides of Bi and Mo, and the catalyst could be used in a fluid bed catalytic reactor. Also, Alundum in ⅛ inch cubes could be coated and used as a catalyst in an exothermic reaction.

We claim:

1. A catalyst comprising (a) an essentially inert, at least partially porous support of at least about 20 microns in diameter, said support having an outer surface, and (b) a coating consisting essentially of (1) a catalytically active oxide material or (2) a catalytically active oxide material and an oxide support material on said outer surface of said inert support which strongly adheres to said outer surface of said inert support.

2. The catalyst of claim 1 wherein the coating is about 10 to about 100 percent by weight of the inert support.

3. The catalyst of claim 1 wherein the inert support is selected from the group consisting of silica, alumina, alumina-silica, silicon carbide, titania and zirconia.

4. The catalyst of claim 1 wherein the catalytically active oxide material is a metal oxide.

5. The catalyst of claim 1 wherein the catalytically active oxide material is selected from oxides of alkali metals, alkaline earth metals, V, Cr, Mo, W, Mn, Fe, Co, Ni, Cu, Zn, In, Tl, Sn, Sb, Bi and As and optionally an oxide of phosphorus.

6. The catalyst of claim 1 wherein the active oxide catalytic material contains at least the oxides of Sb and Mo.

7. The catalyst of claim 1 wherein the active oxide catalytic material contains at least the oxides of V, W and Mo.

8. The catalyst of claim 1 wherein the active catalytic material contains at least the oxides of Bi and Mo.

9. The catalyst of claim 1 wherein the inert support is essentially spherical.

10. A process for making the catalyst of claim 1 comprising the steps of:
  a. contacting an essentially inert support of at least 20 microns in diameter with an excess of liquid in such manner that the liquid is adsorbed by the support to produce a wet support,
  b. drying said wet support to produce a partially wet support, said partially wet support being one that does not have the appearance of liquid on the outer surface of the support, but has at least some liquid adsorbed on the support,
  c. contacting said partially wet support with a powder consisting essentially of (1) a catalytically active oxide material having a particle size of less than about 500 microns or (2) a catalytically active oxide material having a particle size of less than about 500 microns and an oxide support material, and
  d. gently agitating the mixture of partially wet support and catalytically active oxide material to produce an inert support having a strongly adherent coating of (1) catalytically active oxide material or (2) a catalytically active oxide material and an oxide support material.

11. A process for making the catalyst of claim 1 comprising the steps of:
  a. contacting an essentially inert support of at least 20 microns in diameter with a measured amount of liquid to produce a partially wet support, said partially wet support being one that does not have the appearance of liquid on the outer surface of the support, but has at least some liquid adsorbed on the support,
  b. contacting said partially wet support with a powder of (1) a catalytically active oxide material or (2) a catalytically active oxide material and an oxide support material having a particle size of less than about 500 microns, and
  c. gently agitating the mixture of partially wet support and (1) catalytically active oxide material or (2) catalytically active oxide material and an oxide support material to produce an inert support having a strongly adherent coating of the said material.

* * * * *